US007872131B2

(12) United States Patent
Lang et al.

(10) Patent No.: US 7,872,131 B2
(45) Date of Patent: Jan. 18, 2011

(54) METHOD FOR PRODUCING A SOLUTION OF PURE TRIETHYLENEDIAMINE (TEDA)

(75) Inventors: Ortmund Lang, Quirnbach (DE); Matthias Frauenkron, Freinsheim (DE)

(73) Assignee: BASF SE, Ludwigshafen (DE)

( * ) Notice: Subject to any disclaimer, the term of this patent is extended or adjusted under 35 U.S.C. 154(b) by 1106 days.

(21) Appl. No.: 11/579,923

(22) PCT Filed: May 13, 2005

(86) PCT No.: PCT/EP2005/005226

§ 371 (c)(1),
(2), (4) Date: Nov. 8, 2006

(87) PCT Pub. No.: WO2005/111043

PCT Pub. Date: Nov. 24, 2005

(65) Prior Publication Data

US 2008/0021218 A1     Jan. 24, 2008

(30) Foreign Application Priority Data

May 15, 2004   (DE) ...................... 10 2004 024 274

(51) Int. Cl.
   *C07D 487/08* (2006.01)
(52) U.S. Cl. ..................................... 544/352
(58) Field of Classification Search .................. 544/352
   See application file for complete search history.

(56) References Cited

U.S. PATENT DOCUMENTS

| | | | |
|---|---|---|---|
| 3,297,701 A | 1/1967 | Brader et al. | |
| 4,017,494 A | 4/1977 | Bosche et al. | |
| 4,757,143 A | 7/1988 | Vanderpool et al. | |
| 4,804,758 A | 2/1989 | Hoelderich et al. | |
| 5,741,906 A | 4/1998 | Santiesteban et al. | |
| 6,555,688 B1 | 4/2003 | Klockemann et al. | |
| 6,627,756 B1 | 9/2003 | Riechers et al. | |
| 2002/0107394 A1 | 8/2002 | Frauenkron et al. | |
| 2002/0156278 A1 | 10/2002 | Lang et al. | |
| 2003/0004349 A1 | 1/2003 | Lang et al. | |
| 2004/0186291 A1 | 9/2004 | Ciprian et al. | |
| 2004/0220405 A1 | 11/2004 | Lang et al. | |
| 2004/0236106 A1 | 11/2004 | Frauenkron et al. | |

FOREIGN PATENT DOCUMENTS

| | | |
|---|---|---|
| CH | 659 778 A5 | 2/1987 |
| DE | 1 745 627 | 5/1970 |
| EP | 0 111 928 A1 | 6/1984 |
| EP | 0 382 055 A1 | 8/1990 |
| EP | 0 831 096 A2 | 3/1998 |
| EP | 0 842 935 A1 | 5/1998 |
| EP | 0 842 936 A1 | 5/1998 |
| EP | 0 952 152 A2 | 10/1999 |
| EP | 1071717 | 1/2001 |
| EP | 1 192 993 A1 | 4/2002 |

OTHER PUBLICATIONS 93-071101/09 is English abstract of JB-B-3 132 061, Jul. 2, 1991, Tosoh Corp.
93-071102/09 is English abstract of JB-B 3 132 062, Jul. 2, 1991, Tosoh Corp.
93-071103/09 is English abstract of JB-B 3 132 063, Jul. 2, 1991, Tosoh Corp.

*Primary Examiner*—James O Wilson
*Assistant Examiner*—Brian McDowell
(74) *Attorney, Agent, or Firm*—Connolly Bove Lodge & Hutz LPP

(57) ABSTRACT

Process for preparing a solution of pure triethylenediamine (TEDA), in which TEDA is vaporized, the gaseous TEDA is passed into a liquid solvent 1 (quench) and the TEDA is crystallized from the resulting solution and separated off (solid-liquid separation), wherein the crystalline TEDA obtained is dissolved in a solvent 2 and a stripping gas is passed through the resulting solution (stripping).

21 Claims, No Drawings

US 7,872,131 B2

METHOD FOR PRODUCING A SOLUTION OF PURE TRIETHYLENEDIAMINE (TEDA)

This application is the National Phase of International Application No. PCT/EP2005/005226 filed on May 13, 2005; and this application claims priority of Application No. 102004024274.7 filed in Germany on May 15, 2004 under 35 U.S.C. §119; the entire contents of all are hereby incorporated by reference.

The present invention relates to a process for preparing a solution of pure triethylenediamine (TEDA=DABCO®=1,4-diazabicyclo[2.2.2]octane), in which TEDA is vaporized, the gaseous TEDA is passed into a liquid solvent 1 (quench) and the TEDA is crystallized from the resulting solution and separated off (solid-liquid separation).

TEDA is an important intermediate and end product in the chemical industry and is used mainly as such as catalyst in polyurethane production.

In this field of use and others, a pure, virtually odorless TEDA solution which has very low discoloration, e.g. a very small APHA color number (DIN-ISO 6271), and retains these properties even over relatively long storage times (e.g. 6, 12 or more months) is desired.

There are a large number of different syntheses for preparing triethylenediamine (TEDA), and these differ mainly in the choice of starting materials and the catalysts employed.

The zeolite-catalyzed TEDA synthesis is mainly carried out using N-(2-aminoethyl)-piperazine (Tosoh Corp., JP-B-3 132 061, JP-B-3 132 062, JP-B-3 132 063 and EP-A1-1 192 993), ethylenediamine and/or piperazine (Air Products, EP-A1-842 936; BASF AG, EP-A1-382 055, WO 01/02404, EP-A1-1 215 211 and WO 03/004499) as starting materials. Selectivities to TEDA of up to 90% can be achieved using such a method.

The known processes for preparing TEDA lead to formation of crude reaction products which can comprise TEDA together with water, by-products such as piperazine and high molecular weight polymers and also any solvent used in the reaction. TEDA is usually separated off from these mixtures by batchwise or continuous distillation or rectification and generally purified by crystallization or recrystallization in a subsequent step.

Owing to its properties [hygroscopic, temperature-sensitive, boiling point (174° C. at atmospheric pressure) and melting point (158-160° C.) are close together], TEDA is difficult to handle and can be handled only with some engineering outlay without a deterioration in the quality of the TEDA in respect of color, color stability (undesirable increase in the color number, e.g. measured as APHA color number, over the storage time), odor (e.g. undesirable odor of cyclic saturated 5-membered N-heterocycles or other cyclic saturated 6-membered N-heterocycles and/or aromatic 5- or 6-membered N-heterocycles) and purity occurring. A similar situation applies to TEDA solutions.

The earlier German patent application No. 10303696.2 of Jan. 30, 2003 (BASF AG) relates to a process for preparing TEDA solutions comprising a solvent from the group consisting of polyhydric alcohols and ethers of polyhydric alcohols, which process comprises a) passing gaseous TEDA into the solvent and b) treating the solution with one or more suitable adsorbents.

EP-A1-1 070 717 (BASF AG) relates to a process for preparing a solution of pure TEDA, in which TEDA is vaporized and the gaseous TEDA is passed into a liquid solvent 1 (quench), and to a process for preparing pure TEDA by crystallizing the TEDA from this solution.

The crystalline TEDA is separated off from the laden solvent 1 (mother liquor) in a solid-liquid separation and, for example, subsequently dissolved in a second solvent (solvent 2) suitable for further processing of the TEDA.

EP-A-1 223 172, EP-A-1 258 485 and WO-A-03/022851 (all BASF AG) relate to further embodiments of the above-mentioned quench process for preparing TEDA solutions or pure TEDA.

A disadvantage of these processes is that the crystalline TEDA obtained by the above processes can still be contaminated with solvent 1 and secondary components dissolved therein. Virtually complete separation of the solvent 1 from the crystalline TEDA is absolutely necessary for achieving the specification required.

It is an object of the present invention to find an improved, efficient and economical process for preparing pure TEDA solutions which are of improved quality in respect of color, color stability, odor and purity. The yield of TEDA should also be increased.

According to the invention, it has been recognized that the solvent 1 from the crystallization and by-products and decomposition products dissolved in the solvent 1 lead to a reduction in the quality of the TEDA. A reduction in the quality of the TEDA can be prevented by the major part of the solvent 1 and thus also the undesirable secondary components being separated off.

The solvent 1 still present is usually separated off from TEDA in a drying step (e.g. in a dryer). Here, there is a considerable loss of product because of the strong tendency to sublime. Depending on the solvent 1 used, the TEDA loss increases with increasing temperature and rising amount of drying gas. To remove the solvent 1 virtually completely, high temperatures have been set in the drying step, depending on the solvent 1. At about 80° C., there is a transition known from the literature from LT (low-temperature) to HT (high-temperature) TEDA which has a much greater tendency to cake, so that further processing of the TEDA becomes very difficult. n addition, the solvent 1 enclosed in the TEDA crystals during the crystallization and thus also the enclosed undesirable secondary components cannot be removed by customary drying processes.

We have accordingly found a process for preparing a solution of pure TEDA, in which TEDA is vaporized, the gaseous TEDA is passed into a liquid solvent 1 (quench) and the TEDA is crystallized from the resulting solution and separated off (solid-liquid separation), wherein the crystalline TEDA obtained is dissolved in a solvent 2 and a stripping gas is passed through the resulting solution (stripping).

In the process of the invention, the solvent 1 included in the crystals is also liberated as a result of the dissolution of the TEDA crystals and can subsequently be stripped out of the TEDA solution by means of a gas.

After the solid-liquid separation, the TEDA together with the solvent 1 still present is intensively brought into contact with the respective solvent 2 in a mixing apparatus (e.g. a stirred vessel) and dissolved.

The temperature in the dissolution of the TEDA is preferably set to less than/equal to 100° C., preferably from 20 to 60° C. The absolute pressure is preferably from 0.1 to 5 bar, particularly from 0.5 to 1.5 bar.

The solvent 2 is preferably an alcohol, in particular a $C_{2\text{-}13}$-alcohol, and/or an alkyl ether, in particular a $C_{2\text{-}17}$-alkyl ether.

The solvent 2 is preferably a $C_{2\text{-}9}$-diol, $C_{2\text{-}9}$-diol mono($C_{1\text{-}4}$-alkyl)ether, $C_{2\text{-}9}$-diol di($C_{1\text{-}4}$-alkyl)ether, $C_{3\text{-}8}$-triol, $C_{2\text{-}8}$-dialkyl ether and/or $C_{3\text{-}12}$-alicyclic ether, in particular a $C_{2\text{-}6}$-diol, $C_{2\text{-}6}$-diol mono($C_{1\text{-}4}$-alkyl)ether, $C_{2\text{-}6}$-diol di($C_{1\text{-}4}$- alkyl)ether, $C_{3-6}$-triol, $C_{2-6}$-dialkyl ether and/or $C_{4-6}$-alicyclic ether, where $C_{1-4}$-alkyl=methyl, ethyl, n-propyl, isopropyl, n-butyl, isobutyl, tert-butyl.

Very particularly preferred solvents 2 are dipropylene glycol (DPG) (e.g. as isomer mixture), monoethylene glycol (MEG), diethylene glycol (DEG), triethylene glycol (TEG), tripropylene glycol (e.g. as isomer mixture), 1,4-butanediol (BDO), 1,5-pentanediol, 1,6-hexanediol, 1,3-propanediol, 1,2-propanediol, 2,2-dimethyl-1,3-propanediol (neopentyl glycol), dipropylene glycol mono-n-butyl ether, dipropylene glycol mono-tert-butyl ether, dipropylene glycol monomethyl ether, monoethylene glycol monomethyl ether, monoethylene glycol monoethyl ether, monoethylene glycol mono-n-butyl ether, diethylene glycol monomethyl ether, tripropylene glycol monomethyl ether, monoethylene glycol dimethyl ether, monoethylene glycol diethyl ether, diethylene glycol dimethyl ether, diethylene glycol diethyl ether, tripropylene glycol dimethyl ether, glycerol, 1,3,5-pentanetriol, 1,1,1-trimethylolpropane (TMP, 1,1,1-tris(hydroxymethyl)-propane), diethyl ether, di-n-butyl ether, methyl tert-butyl ether, tetrahydrofuran (THF), 1,4-di-oxane.

During or after the dissolution step, the solvent 1 originating from the crystallization is stripped out of the resulting solution by means of gas in the same apparatus as used in the dissolution or another suitable apparatus (e.g.: stirred vessel or column). Mass transfer takes place here. The solvent 1 is preferably carried out with the stripping gas.

It has surprisingly been found that the by-products and decomposition products responsible for the reduction in the quality of the TEDA are likewise stripped out preferentially by the gas.

After the stripping step has been carried out, the TEDA solution can be dispensed for further use, e.g. as commercial product.

The color number of a TEDA solution, e.g. a 33% strength by weight solution in, for example, dipropylene glycol, obtained according to the invention is preferably less than 50 APHA, in particular less than 30 APHA (DIN-ISO 6271). Such a solution preferably has a water content of less than 0.35% by weight and a TEDA purity (calculated without solvent) of greater than 99.90% by weight, in particular greater than 99.95% by weight.

The TEDA solutions obtained according to the invention have no odor arising from secondary components, in particular from cyclic saturated 5-membered N-heterocycles or other cyclic saturated 6-membered N-heterocycles and/or aromatic 5- or 6-membered N-heterocycles.

The TEDA solutions obtained according to the invention preferably have a content of solvent 1 of less than 50 ppm by weight, in particular less than 20 ppm by weight (based on TEDA).

The stripping gas leaving the stripping step, which still comprises TEDA in addition to the solvent 1 from the crystallization step, can be separated into TEDA and gas laden with solvent 1 in a further separation step usually configured as absorption (e.g. by means of water).

The TEDA which has been recovered in this way can be recirculated to the process.

The removal according to the invention of the solvent 1 originating from the crystallization by means of a stripping gas can be carried out by methods and under conditions known to those skilled in the art.

The type of apparatus for stripping is chosen according to what is most advantageous. Preference is given to using vessels, stirred vessels or columns with or without internals. The TEDA solution can be introduced continuously or batchwise. The introduction of stripping gas into the TEDA solution (stripping) can be carried out during or after the dissolution of the TEDA in the solvent 2.

The gas is preferably introduced via a ring nozzle which is preferably located at the bottom of the vessel.

Such ring nozzles are known to those skilled in the art, e.g. from Z. Gao et al., Chemical Engineering Research and Design: 4th International Symposium on Mixing in Industrial Processes (ISMIP-4), 14-16 May 2001, Toulouse, France/ Joel Bertrand, Ed. (2001) 79(A8), 973-978, and Z. D. Chen et al., Chem. Eng. Res. Des. (1999) 77(A2), 104-109, and W. -M. Lu et al., Chem. Eng. J. (Lausanne) (1986) 33(2), 57-62.

Gas velocities in the range from 0.1 to 5 cm/s, in particular from 0.2 to 1 cm/s, (based on the free cross section of the vessel) are preferably set.

The amount of stripping gas used is preferably such that, depending on the amount of stripping gas at the commencement of stripping, offgas having a concentration of the solvent 1 originating from the crystallization of from about 0.1 to 40% by weight, preferably from 1 to 10% by weight, is obtained.

Suitable stripping gases are, particularly, noble gases (helium, neon, argon, xenon), gases comprising noble gases, nitrogen, nitrogen-containing gases, in particular nitrogen-containing gases having a predominant proportion of $N_2$, e.g. air.

Very particular preference is given to nitrogen, in particular $N_2$ having a purity of greater than 99% by volume, very particularly preferably greater than 99.9% by volume.

Stripping is preferably carried out for a period of from 0.1 to 5 hours, in particular from 1 to 3 hours.

The TEDA solution resulting after stripping in the process of the invention comprises less than 1% by weight, preferably less than 0.1% by weight, very particularly preferably less than 0.01% by weight, of the solvent 1 originating from the crystallization.

The temperature during stripping is preferably set to less than/equal to 100° C., particularly from 20 to 70° C., particularly preferably from 40 to 60° C. The absolute pressure is preferably from 0.1 to 5 bar, in particular from 0.5 to 1.5 bar.

As a result of the removal of the solvent 1 present from the crystallization and the recovery of the TEDA in the absorption step, the process of the invention reduces the TEDA losses and gives pure TEDA having the improved yield and purity desired according to the object of the invention.

The TEDA which is used in the process of the invention and is to be vaporized can be obtained by known processes, e.g. by reaction of monoethanolamine, diethanolamine, triethanolamine, ethylenediamine (EDA), diethylenetriamine, triethylenetetramine, piperazine, N-(2-hydroxyethyl)piperazine, N,N'-bis(2-hydroxyethyl)piperazine, N-(2-aminoethyl)piperazine, N,N'-bis(2-aminoethyl)piperazine, morpholine or mixtures thereof over a catalyst [e.g. metal pyrophosphates, metal phosphates (e.g. alkaline earth metal monohydrogenphosphate), zeolites, zirconium phosphates, $Al_2O_3$, $SiO_2$, phosphorus-containing $TiO_2$ or $ZrO_2$] at elevated temperature (preferably from 250 to 450° C.). The absolute pressure here is usually from 0.1 to 50 bar, in particular from 0.1 to 5 bar. The reaction can optionally be carried out in the presence of an inert polar aprotic solvent (e.g. N-alkylpyrrolidone (such as N-methylpyrrolidone), dioxane, THF, dialkylformamide (such as dimethylformamide), dialkylacetamide (such as dimethylacetamide)) and an inert carrier gas (e.g. $N_2$ or Ar).

Such processes are described, for example, in the documents cited at the outset and also in DT-A-24 42 929, U.S. Pat. No. 3,297,701, DE-A-36 34 258, DE-A-1 745 627, DE-A-37 18 395, EP-A-111 928, EP-A-842 935, EP-A-831 096, EP-A-952 152 and U.S. Pat. No. 5,741,906.

The TEDA to be vaporized is preferably prepared continuously from EDA using a zeolite catalyst at a reaction temperature in the range 310-370° C. as described in WO-A-01/02404, with the feed stream comprising 5-80% by weight, in particular 20-70% by weight, very particularly preferably 35-60% by weight, of EDA, having a water content of 2-60% by weight, in particular 10-60% by weight, and the zeolite being of the pentasil type, having an Si:Al atomic ratio of 100-700:1 and being at least partly present in the $H^+$ and/or $NH_4^+$ form.

The feed stream very particularly preferably additionally comprises 1-50% by weight, in particular 10-30% by weight, of PIP.

In the process of the invention, the TEDA is preferably vaporized from a mixture comprising a solvent or diluent having a boiling point at atmospheric pressure (=1.01325 bar) in the range from 175 to 250° C. and the gaseous TEDA is passed into a liquid solvent 1.

The solvent in whose presence the TEDA is vaporized and the solvent into which the gaseous TEDA is passed can be the same solvent or different solvents.

Passing the gaseous TEDA into a liquid solvent (TEDA quench) reduces the formation of undesirable by-products and decomposition products which lead to a reduction in the quality of the TEDA.

The liquid state of TEDA at the outlet of the vaporization apparatus, e.g. rectification or distillation apparatus, is avoided, viz. the liquefaction of the distillate customary in distillations does not take place. Instead, the gaseous TEDA is passed directly into a liquid solvent.

The solvent or diluent present in the mixture from which the TEDA is vaporized preferably has a boiling point at atmospheric pressure in the range from 175 to 250° C., particularly preferably in the range from 180 to 230° C., in particular in the range from 190 to 210° C.

As solvent or diluent present in the mixture from which the TEDA is vaporized, the following substances are particularly useful:

- inert, polar aprotic solvents [e.g. alkyl-2-pyrrolidones (such as N-methyl-2-pyrrolidone (NMP), 1-ethyl-2-pyrrolidone (NEP), 1,5-dimethyl-2-pyrrolidone, 1-isopropyl-2-pyrrolidone), ethers (such as diethylene glycol diethyl ether, triethylene glycol dimethyl ether, triethylene glycol diethyl ether), ketones (such as acetophenone, propiophenone), lactones (such as γ-butyrolactone), sulfoxides (such as dimethyl sulfoxide), carboxylic esters (such as dimethylfumarate), nitriles (such as benzonitrile) and ureas (such as 1,3-dimethylimidazolidin-2-one (DMEU), tetramethylurea)],
- inert, cyclic or acyclic hydrocarbons, in particular saturated cyclic or acyclic hydrocarbons (e.g. undecane, dodecane, cis-decalin, trans-decalin),
- inert, chlorinated aliphatic hydrocarbons (e.g. 1-chlorooctane, 1,1-dichlorooctane),
- inert aromatic hydrocarbons, nitroaromatics and phenols (e.g. naphthalene, n-butylbenzene, phenol, cresol, nitrobenzene, nitrophenol),
- inert, chlorinated aromatic hydrocarbons (e.g. 1,2-dichlorbenzene, benzyl chloride, 1,2,3,4-tetramethylbenzene, 1,2,3,5-tetramethylbenzene),
- inert alcohols (e.g. benzyl alcohol, 2-ethylhexanol, 1-octanol, isodecanol, 1,2-propanediol, 1,3-propanediol, ethylene glycol, diethylene glycol, 1,2-propylene glycol, 1,3-propylene glycol, 1,2-butanediol, 1,3-butanediol, 2,3-butanediol, 1,4-butanediol, neopentyl glycol, diethylene glycol monomethyl ether, dipropylene glycol),
- inert, primary, secondary and tertiary amines (e.g. tri-n-butylamine, benzylamine, aniline, N-ethylaniline, N,N-dimethylaniline, N,N-diethylaniline),
- inert N-alkylamides (e.g. N-methylformamide, N-methylacetamide) and mixtures thereof.

Particular preference is given to polar aprotic solvents or diluents having an $E^N_T$ of from 0.1 to 0.6, particularly preferably from 0.2 to 0.5, in particular from 0.3 to 0.45. (For the definition of $E^N_T$, see Ch. Reichardt, Solvents and solvent effects in organic chemistry, 2nd Edition, VCH 1988).

Very particularly preferred solvents here are NMP and monoethylene glycol.

The solvent or diluent present in the mixture from which the TEDA is vaporized is preferably added to the crude or still contaminated TEDA after the synthesis of the TEDA. Introduction of the solvent into the bottom of the column in the TEDA distillation is advantageous.

The solid or diluent can be used in a single pass or as a circulating solution after the high boilers have been separated off.

The procedure is preferably such that, depending on the type of solvent or diluent, solutions or mixtures having a TEDA content of from about 1 to 90% by weight, preferably from 40 to 70% by weight, are obtained.

The vaporization of the TEDA, if appropriate from the mixture comprising a solvent or diluent, can be carried out by methods and under conditions with which those skilled in the art are familiar, e.g. by simple vaporization from crude TEDA (pot vaporization), or preferably in a distillations or rectification apparatus, with the TEDA or a mixture comprising the TEDA (crude TEDA), optionally together with the solvent or diluent, being initially charged.

The gaseous TEDA is preferably obtained at the top or at a side offtake of a distillation column. The gaseous TEDA preferably has a purity of greater than 90% by weight, particularly preferably greater than 95% by weight, in particular greater than 97% by weight.

The residence time and thus the thermal stress in the work-up of the TEDA by distillation is advantageously kept low by constructional measures on columns and/or vaporizers (e.g.: minimization of the volume of liquid phase) and/or by use of thermally gentle evaporation processes (e.g.: falling film evaporators, thin film evaporators).

The temperature of the mixture comprising TEDA and the solvent or diluent from which the TEDA is vaporized (e.g. the bottoms from the corresponding TEDA distillation column) is preferably set to $\leq 230°$ C., preferably from 190 to 210° C., by choice of the solvent or diluent to be used, the TEDA content of the mixture and/or the pressure. The absolute pressure is preferably from 0.1 to 5 bar, in particular from 0.5 to 1.5 bar.

The time interval between the time when the gaseous TEDA is obtained and the time when the TEDA is quenched is advantageously $\leq 10$ seconds.

Particularly suitable solvents 1 for the TEDA quench are cyclic or acyclic (=aliphatic) hydrocarbons (in particular branched or unbranched alkanes or alkane mixtures), e.g. n-pentane, isopentane, cyclopentane, n-hexane, cyclohexane, n-heptane, n-octane, petroleum ether (PE) (e.g. PE 30/60, 35/60, 40/60), chlorinated aliphatic hydrocarbons (in particular chlorinated alkanes, such as dichloromethane, trichloromethane, dichloroethane, trichloroethane), aromatic hydrocarbons (e.g. benzene, toluene, xylenes), chlorinated aromatic hydrocarbons (e.g. chlorobenzene), alcohols, in particular $C_{1-4}$-alcohols (e.g. methanol, ethanol, n-propanol), ketones, in particular $C_{3-6}$-ketones (in particular aliphatic ketones, such as acetone, methyl ethyl ketone, diethyl ketone), aliphatic carboxylic esters (e.g. methyl acetate, ethyl acetate), aliphatic nitriles (e.g. acetonitrile, propionitrile), ethers (e.g. dioxane, THF, diethyl ether, methyl tert-butyl ether, ethylene glycol dimethyl ether)

and mixtures thereof.

As solvent 1 for the TEDA quench, preference is given to using an aliphatic hydrocarbon, in particular a saturated aliphatic hydrocarbon having from 5 to 8 carbon atoms (e.g. n-pentane, isopentane, cyclopentane, n-hexane, cyclohexane, n-heptane or mixtures thereof, e.g. petroleum ether), ethanol, toluene and/or acetone.

The crystallization of the pure TEDA from the TEDA solution obtained can be carried out by the methods known to those skilled in the art. The TEDA crystals obtained by a subsequent multistage, or preferably single-stage, crystallization are highly pure (purity of preferably at least 99.5% by weight, in particular at least 99.9% by weight) and the color number of a 33% strength by weight solution, e.g. in dipropylene glycol, is preferably less than 50 APHA (DIN-ISO 6271), in particular less than 30 APHA.

The introduction of the gaseous TEDA into the liquid solvent is carried out in a quenching apparatus, e.g. preferably in a falling-film condenser (thin-film condenser, trickle-film condenser or falling-stream condenser) or in a nozzle apparatus. The gaseous TEDA can be conveyed in cocurrent or in countercurrent to the liquid solvent.

The gaseous TEDA is advantageously introduced from above into the quenching apparatus. Also advantageous is tangential introduction of the liquid solvent at the top of the falling film condenser or introduction of the liquid solvent through one or more nozzles in order to achieve complete wetting of the interior wall of the quenching apparatus.

The solvent for the TEDA quench can be used in a single pass or as circulating solution.

The amount of solvent 1 used in the TEDA quench is preferably such that, depending on the type of solvent, solutions having a TEDA content of from about 1 to 50% by weight, preferably from 20 to 40% by weight, are obtained.

The temperature in the TEDA quench is preferably set by bringing the temperature of the solvent used and/or the quenching apparatus to from 20 to 100° C., preferably from 30 to 60° C.

The absolute pressure in the TEDA quench is preferably from 0.5 to 1.5 bar.

Due to the partial vaporization of the solvent used in the TEDA quench as a result of the introduction of heat by the gaseous TEDA, the gas space in the quenching apparatus is saturated with solvent vapor. This significantly reduces or completely prevents desublimation of the gaseous TEDA and the resulting blockage problems caused by deposition of solids in the apparatus and/or in the outflow lines.

In a preferred embodiment, the process of the invention can be carried out as follows:

A mixture comprising TEDA, which has been obtained, for example, as reactor output in a continuous process for the reaction of ethylenediamine and piperazine in a gas-phase reactor at from 320 to 420° C. and from 0.5 to 1.5 bar (abs.) in the presence of a solvent (e.g. water), a carrier gas (e.g. $N_2$ or Ar) and a zeolite catalyst (e.g. as described in WO-A-01/02404), is fed into a distillation apparatus comprising a distillation column having, for example, about 15 theoretical plates. Here, low boilers (e.g. ammonia, ethylamine, water) are separated off overhead at a temperature at the top of from 95 to 120° C. and an absolute pressure of preferably from 500 mbar to 1.5 bar. The bottoms are pumped into a further distillation column having, for example, about 30 theoretical plates. At a temperature at the top of from 140 to 160° C. and an absolute pressure of preferably from 500 mbar to 1.5 bar, piperazine is separated off overhead in this column and optionally returned to the synthesis reactor.

The bottoms comprising TEDA and high boilers are pumped into a further distillation column having, for example, about 25 theoretical plates. At an absolute pressure of preferably from 500 mbar to 1.5 bar, the high boilers are discharged via the bottoms in this column. At the top of the column, TEDA having a purity of greater than 95% by weight, in particular greater than 97% by weight, is taken off in gaseous form via a partial condenser and is cooled very quickly and simultaneously dissolved directly in a solvent 1 (e.g. pentane, cyclohexane) at a temperature of preferably from 30 to 100° C., particularly from 30 to 60° C., in a falling film condenser (TEDA quench).

After the TEDA quench, TEDA is crystallized from the solution in a crystallization step by evaporation of the solvent at a temperature preferably from 10 to 100° C., particularly from 20 to 40° C., and at a pressure of preferably from 0.1 to 5 bar, particularly from 0.5 to 1.5 bar, or by cooling at a temperature of preferably from −10 to 40° C., particularly from 0 to 10° C.

The suspension taken off from the crystallizer is separated into TEDA and mother liquor in a solid-liquid separation, e.g. in a centrifuge. The mother liquor, which still comprises residues of the desired product, is then intensively brought into contact with an extractant (e.g. water) at a temperature of preferably from 10 to 100° C., particularly from 20 to 40° C., and at an absolute pressure preferably from 0.1 to 5 bar, particularly from 0.5 to 1.5 bar, in an extraction stage (e.g. extraction column).

The extract phase which leaves the extraction stage after mass exchange and phase separation, and which comprises most of the TEDA and the undesirable by-products and decomposition products which lead to a reduction in the quality of the TEDA, is conveyed back to the reactor or to the distillation. The raffinate phase, which comprises only traces of TEDA, is recirculated to the TEDA quench.

The TEDA obtained from the solid-liquid separation, which still contains residues of the solvent 1 used in the crystallization (e.g. pentane, cyclohexane) and the by-products and decomposition products responsible for the reduction in the quality of the TEDA, is dissolved in a solvent 2 (e.g. dipropylene glycol, monoethylene glycol or 1,4-butanediol) in a mixing apparatus (e.g. stirred vessel). The temperature in the dissolution of the TEDA is preferably set to less than/equal to 100° C., particularly from 20 to 60° C. The absolute pressure here is preferably from 0.1 to 5 bar, particularly from 0.5 to 1.5 bar.

To separate off the solvent 1 by means of a stripping gas, the solution is intensively brought into contact with a gas (e.g. nitrogen) at a temperature of preferably from 10 to 100° C., particularly preferably from 20 to 70° C., in particular from 40 to 60° C., and at an absolute pressure of preferably from 0.1 to 5 bar, particularly preferably from 0.5 to 1.5 bar (stripping). Here, the solvent 1 and the undesirable secondary components are preferentially taken up by the stripping gas and separated off from the TEDA solution.

EXAMPLES

Example 1

Comparative Example

The TEDA obtained for the solid-liquid separation, which had a pentane content (solvent 1) of about 2000 ppm by weight, was dried for about two hours at 45° C./1 $bar_{abs}$ in a rotary evaporator. The pentane content could be reduced only to about 400 ppm by weight in this way. The TEDA loss was about 10% by weight. Prolonging the drying time and/or increasing the temperature led to no appreciable reduction in the pentane content but to significantly higher TEDA losses.

Example 2

According to the Invention

The experiment was carried out as described in Example 1, but the TEDA obtained after the solid-liquid separation was dissolved in dipropylene glycol (=solvent 2) at 50° C. in a stirred vessel and subsequently stripped by means of nitrogen (700 liter/h) at 50° C. The gas was introduced at a gas velocity of 0.6 cm/s (based on the free cross section of the vessel) via a ring nozzle at the bottom of the vessel. After a stripping time of two hours, the pentane content (=solvent 1) was less than 10 ppm by weight (based on TEDA). The TEDA loss was <1% by weight.

The invention claimed is:

1. A process for preparing a solution of pure triethylenediamine (TEDA), comprising the steps in which TEDA is vaporized, the gaseous TEDA is passed into a liquid solvent 1 (quench) and the TEDA is crystallized from the resulting solution and separated off (solid-liquid separation), wherein the crystalline TEDA obtained is dissolved in a solvent 2 and a stripping gas is passed through the resulting solution (stripping), with solvent 1 being liberated and subsequently stripped from the TEDA solution by means of the stripping gas.

2. The process according to claim 1, wherein the stripping gas is nitrogen, a noble gas, a nitrogen-containing gas or a gas comprising noble gas.

3. The process according to claim 1, wherein the solvent 2 is an alcohol and/or alkyl ether.

4. The process according to claim 1, wherein the solvent 2 is a $C_{2-9}$-diol, $C_{2-9}$-diol mono($C_{1-4}$-alkyl) ether, $C_{2-9}$-diol di($C_{1-4}$-alkyl) ether, $C_{3-8}$-triol, $C_{2-8}$-dialkyl ether and/or $C_{3-12}$-alicyclic ether.

5. The process according to claim 1, wherein the solvent 2 is dipropylene glycol, monoethylene glycol and/or 1,4-butanediol.

6. The process according to claim 1, wherein stripping is carried out at a temperature in the range from 20° C. to 100° C.

7. The process according to claim 1, wherein stripping is carried out at a temperature in the range from 40° C. to 60° C.

8. The process according to claim 1, wherein stripping is carried out at an absolute pressure in the range from 0.1 to 5 bar.

9. The process according to claim 1, wherein the stripping gas is introduced via a ring nozzle.

10. The process according to claim 1, wherein the stripping gas velocity is from 0.1 to 5 cm/s based on the free cross section of the vessel.

11. The process according to claim 1, wherein the stripping gas leaving the stripping step has a concentration of the solvent 1 in the range from 0.1 to 40% by weight.

12. The process according to claim 1, wherein TEDA present in the stripping gas leaving the stripping step is recovered by absorption.

13. The process according to claim 1, wherein the TEDA solution resulting after stripping has a content of solvent 1 of less than 1% by weight.

14. The process according to claim 1, wherein the TEDA solution resulting after stripping has a content of solvent 1 of less than 0.1% by weight.

15. The process according to claim 1, wherein the gaseous TEDA is obtained at the top or at a side offtake of a distillation column.

16. The process according to claim 1, wherein the TEDA is vaporized from a mixture comprising a solvent or diluent having a boiling point at atmospheric pressure in the range from 175 to 250° C.

17. The process according to claim 1, wherein the liquid solvent 1 is selected from the group consisting of cyclic and acyclic hydrocarbons, chlorinated aliphatic hydrocarbons, aromatic hydrocarbons, alcohols, ketones, aliphatic carboxylic esters, aliphatic nitriles and ethers.

18. The process according to claim 1, wherein the liquid solvent 1 (quench solvent) is selected from the group consisting of n-pentane, isopentane, n-hexane, cyclohexane, petroleum ether, ethanol, acetone, toluene and mixtures thereof.

19. The process according to claim 1, wherein the gaseous TEDA to be passed into the liquid solvent 1 (quench) has a purity of greater than 95% by weight.

20. The process according to claim 1, for preparing a solution of TEDA having a TEDA purity, calculated without solvent, of greater than 99.90% by weight.

21. The process according to claim 1, for preparing a solution of TEDA having a content of solvent 1 of less than 50 ppm by weight based on TEDA.

* * * * *